US012029917B2

(12) United States Patent
Verhaegen et al.

(10) Patent No.: US 12,029,917 B2
(45) Date of Patent: Jul. 9, 2024

(54) ENDORECTAL PROBE DEVICE FOR EFFECTING RADIATION TREATMENT OF COLORECTAL CANCEROUS TISSUE IN THE RECTUM OF A HUMAN OR ANIMAL SUBJECT

(71) Applicants: Universiteit Maastricht, Maastricht (NL); Academisch Ziekenhuis Maastricht, Maastricht (NL); Stichting Maastricht Radiation Oncology "Maastro-Clinic", Maastricht (NL)

(72) Inventors: Frank Verhaegen, Maastricht (NL); Murillo Bellezzo, Maastricht (NL); Evert Van Limbergen, Maastricht (NL); Maaike Berbee, Maastricht (NL); Brigitte Reniers, Maastricht (NL); Gabriel Paiva Fonseca, Maastricht (NL)

(73) Assignees: UNIVERSITEIT MAASTRICHT, Maastricht (NL); STICHTING MAASTRICHT RADIATION ONCOLOGY MAASTRO CLINIC, Maastricht (NL); ACADEMISCH ZIEKENHUIS MAASTRICHT, Maastricht (NL)

( * ) Notice: Subject to any disclaimer, the term of this patent is extended or adjusted under 35 U.S.C. 154(b) by 0 days.

(21) Appl. No.: 18/047,070

(22) Filed: Oct. 17, 2022

(65) Prior Publication Data

US 2023/0146314 A1 May 11, 2023

Related U.S. Application Data

(63) Continuation of application No. 16/468,058, filed as application No. PCT/EP2017/083097 on Dec. 15, 2017, now Pat. No. 11,497,933.

(51) Int. Cl.
*A61N 5/10* (2006.01)

(52) U.S. Cl.
CPC ......... *A61N 5/1002* (2013.01); *A61N 5/1007* (2013.01); *A61N 2005/1008* (2013.01);
(Continued)

(58) Field of Classification Search
CPC ............... A61N 5/1002; A61N 5/1007; A61N 2005/1008; A61N 2005/1024; A61N 2005/1025
(Continued)

(56) References Cited

U.S. PATENT DOCUMENTS 3,224,432 A 12/1965 Billingsley
4,584,991 A 4/1986 Tokita
(Continued)

FOREIGN PATENT DOCUMENTS

DE 3823604 A1 1/1990
EP 2335778 A1 6/2011
GB 857992 A 1/1961

OTHER PUBLICATIONS

EPO, Examination Report in European Application No. 17818544.3, dated Nov. 10, 2020, 5 pages.

*Primary Examiner* — Samuel G Gilbert
(74) *Attorney, Agent, or Firm* — Harness, Dickey & Pierce, P.L.C.

(57) ABSTRACT

The invention relates to the radiation treatment of colorectal cancerous tissue in the rectum of a human or animal subject. In particular the invention relates to an endorectal probe device for effecting radiation treatment of colorectal cancerous tissue in the rectum of a human or animal subject. Furthermore the invention relates to an afterloading apparatus for effecting radiation treatment of colorectal cancerous tissue in the rectum of a human or animal subject using
(Continued)

Figure 1:
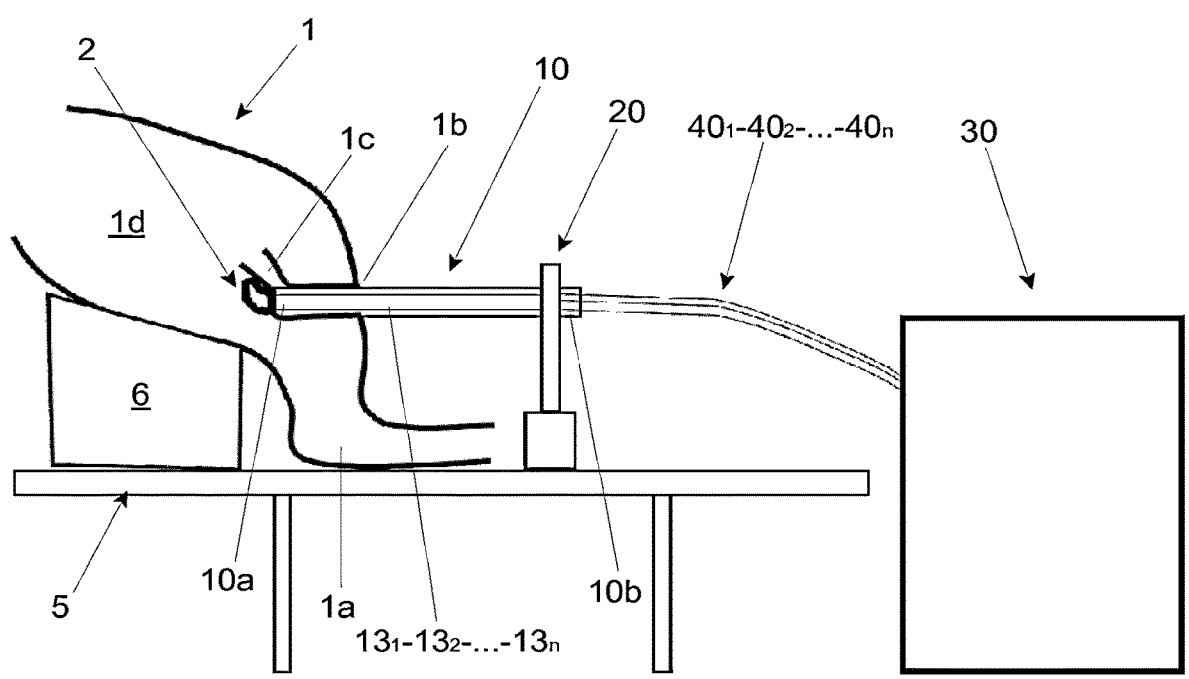

an endorectal probe device according to the invention. Moreover the invention relates to a method for effecting radiation treatment of colorectal cancerous tissue in the rectum of a human or animal subject, wherein the method implements the endorectal probe device according to the invention.

19 Claims, 14 Drawing Sheets

(52) U.S. Cl.
CPC .............. *A61N 2005/1024* (2013.01); *A61N 2005/1025* (2013.01)

(58) Field of Classification Search
USPC .......................................................... 600/3
See application file for complete search history.

(56) References Cited

U.S. PATENT DOCUMENTS

| | | | |
|---|---|---|---|
| 4,657,024 A * | 4/1987 | Coneys | A61M 25/0108 604/523 |
| 5,653,683 A | 8/1997 | D'Andrea | |
| 5,924,973 A | 7/1999 | Weinberger | |
| 6,283,910 B1 | 9/2001 | Bradshaw | |
| 6,440,061 B1 * | 8/2002 | Wenner | A61B 17/3421 600/114 |
| 2004/0249367 A1 | 12/2004 | Saadat | |
| 2006/0020156 A1 | 1/2006 | Shukla | |
| 2008/0146863 A1 | 6/2008 | Stillwagon | |
| 2009/0234178 A1* | 9/2009 | Lebovic | A61N 5/1016 600/6 |
| 2014/0179979 A1 | 6/2014 | Finkelstein | |
| 2016/0213312 A1* | 7/2016 | Singh | A61M 5/007 |
| 2017/0173362 A1 | 6/2017 | Lamoureux | |
| 2019/0329066 A1* | 10/2019 | Lim | A61N 5/1007 |

* cited by examiner

ENDORECTAL PROBE DEVICE FOR EFFECTING RADIATION TREATMENT OF COLORECTAL CANCEROUS TISSUE IN THE RECTUM OF A HUMAN OR ANIMAL SUBJECT

CROSS-REFERENCE TO RELATED APPLICATIONS

This application is a continuation of, and claims priority under 35 U.S.C. § 120 to U.S. application Ser. No. 16/468,058, filed Jun. 10, 2019, which claims priority under 35 U.S.C. § 371 to International Application No. PCT/EP2017/083097, which has an international filing date of Dec. 15, 2017, and which designated the United States of America, which claims priority to European Patent Application No. 16204735.1, filed Dec. 16, 2016, the entire contents of each of which are incorporated herein by reference.

FIELD OF THE INVENTION

The invention relates to the radiation treatment of colorectal cancerous tissue in the rectum of a human or animal subject.

In particular the invention relates to an endorectal probe device for effecting radiation treatment of colorectal cancerous tissue in the rectum of a human or animal subject.

Furthermore the invention relates to an afterloading apparatus for effecting radiation treatment of colorectal cancerous tissue in the rectum of a human or animal subject using an endorectal probe device according to the invention.

Moreover the invention relates to a method for effecting radiation treatment of colorectal cancerous tissue in the rectum of a human or animal subject, wherein the method implements the endorectal probe device according to the invention.

BACKGROUND OF THE INVENTION

Colorectal cancer, also known as bowel cancer, is the development of cancer from the colon or rectum (which are parts of the large intestine) of human but also animal subjects. It is due to the abnormal growth of cells that have the ability to invade or spread to other parts of the body. Signs and symptoms hinting at the development of or already suffering from colorectal cancer may include the presence of blood in the stool, a change in bowel movements, weight loss, and feeling tired all the time.

Most colorectal cancers are due to old age and lifestyle factors with only a small number of cases due to underlying genetic disorders. Some risk factors include diet, obesity, smoking, and lack of physical activity. Dietary factors that increase the risk include red and processed meat as well as alcohol. Another risk factor is inflammatory bowel disease, which includes Crohn's disease and ulcerative colitis. Colorectal cancer typically starts as a benign tumor, often in the form of a polyp, which over time becomes cancerous.

A common therapy of rectal cancer includes surgical resection of the tumor, which might require a general anesthesia of the subject to be treated. Depending on tumor characteristics patients may receive (chemo)radiotherapy before surgery in order to reduce the recurrence rate. Trials have shown that in patients with a complete response after neo-adjuvant treatment, omission of surgery with follow-up (wait and see) might be considered instead of surgery. This is beneficial for the patient, as surgery leads frequently to side effects or the need to have a stoma implanted.

With the currently used radiation dose about 10-20% of all patients will have a complete response after chemoradiotherapy, as increasing the radiation dose will increase the number of patients with a complete response, who do not need to be operated on. Furthermore, in patients who are unfit for surgery, such as elderly patients, increasing the radiation dose will prevent or postpone the occurrence of complaints caused by tumor regrowth.

In case of radiotherapy of rectal cancer tumors cancer patients are mostly treated with externally applied radiation beams. However external beam radiotherapy is not the most suitable technique to provide dose escalation, as these beams have to cross much healthy tissue to deliver their radiation dose to the tumor. In doing so, the radiation damages the healthy tissue, in particular organs of the reproductive system, and as a consequence the dose to the tumor is limited by the dose to the healthy tissue, to avoid radiotherapy side effects such as rectal bleeding and proctitis.

Yet another therapy involves internally applied radiation beams, also called contact x-ray brachytherapy. This treatment is recommended for patients, who are not fit enough for general anesthesia or who do not want major surgery and formation of a stoma. Hereby, an x-ray tube is inserted in the rectum until near the tumor site, and the tumor is exposed to a high local radiation dose. A disadvantage is that there is no clear information on the total dose being delivered, and as such also healthy tissue surrounding the tumor site is being exposed to radiation. Also the radiation equipment used is very expensive.

Another therapy also involving internally applied radiation beams employs an applicator that allows a radioactive $^{192}$Ir source to be introduced, and positioned close to the tumor site. Unfortunately the current designs of this applicator do not allow accurate positioning of the radioactive $^{192}$Ir source with respect to the tumor. Next to an inaccurate positioning as well as an inadequate shielding from healthy tissue and/or directing of radiation to the intended treatment site, such therapy treatments still result in an unnecessary high radiation exposure to a large volume of healthy tissue surrounding the tumor site, causing for a disproportional amount of side effects compared to the intended and desired treatment effect. As such the radiation dose to be administered to the tumor is too limited.

SUMMARY OF THE INVENTION

The invention aims to provide an improved treatment technique based on contact HDR (High Dose Rate) brachytherapy, which implements a novel applicator device for insertion into the rectum, allowing a more accurate positioning of the applicator with respect to the cancerous tumor site in the rectum and also a more accurate radiation dose delivery towards the tumor site, having a dose distribution being more conformal to the geometry of the tumor to be treated, thereby avoiding any (over)exposure of healthy tissue surrounding the tumor site to radiation. By repeating the radiation treatment multiple times over a certain period of time, the tumor irradiated likewise multiple times, which will ultimately result in a complete response.

Hereto an endorectal probe device for effecting radiation treatment of colorectal cancerous tissue in the rectum of a human or animal subject is proposed, the endorectal probe device comprising:

an endorectal catheter probe having an elongated body with a distal probe end and a proximal probe end, which endorectal catheter probe being arranged to be inserted with its proximal probe end within the rectum towards the colorectal cancerous tissue site in the rectum;

the elongated body of the endorectal catheter probe having at least one longitudinal catheter bore extending from the distal probe end towards the proximal probe end, the at least one longitudinal catheter bore being arranged in guiding an energy emitting source towards the colorectal cancerous tissue site for delivering a certain pre-planned amount of radiation energy at one or more pre-determined dwell positions near or at the colorectal cancerous tissue site; as well as an endorectal tube having a hollow elongated body with a distal tube end and a proximal tube probe end, which hollow endorectal tube being arranged to be inserted with its proximal tube end within the rectum and against the colorectal cancerous tissue site in the rectum, and the hollow endorectal tube being arranged in movable accommodating the endorectal catheter probe.

Herewith the endorectal probe device allows for a proper and correct positioning directly against or around the cancerous tumor site in the rectum tissue wall. As such a more accurate radiation treatment can be envisaged, as with this orientation of the probe device against or around the cancer tumor, the tumor cells are directly exposed to the radiation being emitted by the energy emitting source. Thus the tumor is exposed with a radiation dose distribution which is more conformal to the tumor geometry. Also exposure of healthy tissue surrounding the tumor is avoided, thus reducing the side effects for the patient. By repeating the radiation treatment multiple times over a certain period of time, the tumor irradiated likewise multiple times, which will ultimately result in a complete response.

In particular the catheter probe is movable in at least longitudinal direction within the endorectal tube, thus allowing for a proper positioning and orientation directly against the tumor to be treated.

In an embodiment which allows for visual inspection of the orientation of the endorectal tube relative to the tumor site, the proximal tube end of the hollow endorectal tube is open. Herewith, repositioning of the proximal tube end is possible, until the open proximal tube end is properly placed against and/or around the cancerous tumor site to be treated.

Furthermore the proximal probe end of the endorectal catheter probe is closed. As such the closed proximal probe end of the endorectal catheter probe, once inserted into the hollow endorectal tube, can be properly positioned or even pressed against the tumor to be treated, and the energy emitting source can be positioned at a dwell position within the at least one longitudinal catheter bore at a close distance to the tumor site. This allows maximum exposure of the tumor to radiation being emitted by the energy emitting source, whilst avoiding unnecessary and undesired exposure of healthy tissue surrounding the tumor.

In a suitable embodiment, which allows for a direct placement of the catheter probe inside the endorectal tube against the cancerous tumor to be treated, the end face of the closed proximal probe end of the endorectal catheter probe consists of a flat surface. In yet another version the flat end face of the closed proximal probe end exhibits a perpendicular or inclined orientation relative to the longitudinal direction of the endorectal catheter probe. This allows for accurate positioning of the proximal end of the endorectal probe device against the tumor surface if this is not possible with a flat probe end due to the anatomical situation within the patient.

In another embodiment the end face of the closed proximal probe end of the endorectal catheter probe consists of a convex or concave surface. In particular in the concave configuration the concave shaped end face of the closed proximal probe end allows for a direct placement of the endorectal catheter probe against and around the tumor site, wherein the cancer tumor is advantageously surrounded or enveloped. This treatment configuration in particular allows for a direct maximum exposure of the tumor to radiation being emitted by the energy emitting source, whilst avoiding unnecessary and undesired exposure of healthy tissue surrounding the tumor.

In particular the elongated body of the endorectal catheter probe comprises multiple longitudinal catheter bores. With this particular embodiment a proper dose distribution plan can be established prior to the treatment and the treatment is subsequently performed by inserting the energy emitting source at different dwell positions and during corresponding dwell times in the subsequent plurality of catheter bores. Herewith it is established that the tumor is exposed with a radiation dose distribution which is more, in fact nearly as, conformal to the tumor geometry. By repeating the radiation treatment multiple times over a certain period of time, the tumor irradiated likewise multiple times, which will ultimately result in a complete response.

In an embodiment the multiple longitudinal catheter bores are arranged in an equidistant manner around the central axis of the elongated body, in particular in a circle wise manner, whereas the multiple longitudinal catheter bores extend parallel to each other through the elongated body.

In yet another embodiment near the proximal end of the endorectal catheter probe the multiple longitudinal catheter bores diverge from each other. Herewith an accurate positioning of an energy emitting source within a catheter bore near or at the proximal end surface of the catheter probe in dependence on the tumor's geometry is envisaged.

In particular the endorectal catheter probe is transparent to visible light and the radiation used for effecting the radiation treatment, which allows for a visual inspection of the endorectal probe device within the rectum, relative to the tumor site.

In order to avoid undesired and unnecessary exposure of healthy tissue surrounding the tumor site, the proximal tube end and/or the proximal probe end is at least partly opaque to the radiation used for effecting the radiation treatment. Herewith a more accurate direction of radiation solely to the tumor site is obtained.

In particular the proximal tube end and/or the proximal probe end can be provided with one or more insert parts made of an opaque material, such as lead or tungsten. Herewith, any radiation being emitted towards undesired directions, in particular towards healthy tissue regions is effectively blocked/shielded.

Preferably at least the endorectal tube is made of a rigid material, wherein the elongated body of the endorectal tube also may have a straight orientation.

As suitable dimensions for the endorectal probe device according to the invention the endorectal catheter probe may have a diameter of 20-30 mm and a length of 200-250 mm, with the catheter bores having a diameter of approx. 2-3 mm.

For effecting the radiation treatment the at least endorectal catheter probe can be connected with its distal probe end to an afterloading apparatus, wherein the at least one energy emitting source is contained in the afterloading apparatus and is arranged to be inserted through at least one longitudinal catheter bore of said endorectal catheter probe towards the one or more pre-determined dwell positions near or at the colorectal cancerous tissue site using a source wire having a proximal end connected to the energy emitting source.

The afterloading apparatus for effecting radiation treatment of colorectal cancerous tissue in the rectum of a human or animal subject according to the invention and using an endorectal probe device according to the invention, said afterloading apparatus at least comprising:

coupling means for coupling at least the distal end of the endorectal catheter probe to the afterloading apparatus;

insertion means for inserting at least one energy emitting source contained in the afterloading apparatus through at least one longitudinal catheter bore of said endorectal catheter probe towards one or more pre-determined dwell positions near or at the colorectal cancerous tissue site.

As such a more accurate radiation treatment plan can be envisaged, as with an afterloading apparatus implementing an endorectal probe device according to the invention a tumor in the rectum can be properly treated with radiation, and in particular is exposed with a radiation dose distribution which is more, in fact nearly as, conformal to the tumor geometry. Also exposure of healthy tissue surrounding the tumor is avoided, and the patient will not suffer from side effects.

In order to achieve such a radiation treatment plan, wherein the colorectal cancer tumor is treated with a radiation dose distribution which is more, in fact nearly as, conformal to the tumor geometry the afterloading apparatus further comprises:

processing means arranged to generate a radiation treatment plan containing at least information on:
  the human or animal subject to be treated;
  the overall radiation dose to be emitted;
  the energy emitting source to be used;
  the one or more longitudinal catheter bores of the endorectal catheter probe through which the energy emitting source is to be inserted;
  the dwell positions for each of the one or more longitudinal catheter bores at which the energy emitting source is to be positioned; and
  the dwell times corresponding to each dwell positions at which the energy emitting source is to be positioned.

The invention also relates to a method for effecting radiation treatment of colorectal cancerous tissue in the rectum of a human or animal subject, wherein the method implements the endorectal probe device according to the invention, and the method comprising the treatment steps of:

A positioning the human or animal subject on a treatment table;

B inserting the hollow endorectal tube with its proximal tube end within the rectum and against or around the colorectal cancerous tissue site in the rectum;

C fixating the hollow endorectal tube relative to the body of the human or animal subject;

D inserting the endorectal catheter probe with its proximal probe end via the distal tube end in the hollow endorectal tube towards and against the colorectal cancerous tissue site in the rectum;

E fixating the endorectal catheter probe relative to the body of the human or animal subject;

F coupling at least the distal end of the endorectal catheter probe to the afterloading apparatus;

G inserting the at least one energy emitting source contained in the afterloading apparatus through at least one longitudinal catheter bore of said endorectal catheter probe towards one or more pre-determined dwell positions near or at the colorectal cancerous tissue site;

H effecting radiation treatment during a pre-determined dwell time at each of the one or more pre-determined dwell positions;

I retracting the at least one energy emitting source from the at least one longitudinal catheter bore back into the afterloading apparatus.

According to these treatment steps a more accurate radiation treatment can be envisaged, as with this orientation of the probe device against or around the cancer tumor, the tumor cells are directly exposed to the radiation being emitted by the energy emitting source. Thus the tumor is exposed with a radiation dose distribution which is more, in fact nearly as, conformal to the tumor geometry. Also exposure of healthy tissue surrounding the tumor is avoided, and the patient will suffer less from side effects.

The treatment method is furthermore improved, as step D is preceded by the steps:

C1 visualizing the proximal tube end relative to the colorectal cancerous tissue site in the rectum; and C2 repositioning the proximal tube end against or around the colorectal cancerous tissue site in the rectum based on the visualizing step C1.

These additional treatment steps allows for a proper repositioning of the proximal tube end prior to the radiation treatment, until the open proximal tube end is properly placed against and/or around the cancerous tumor site in the rectum tissue wall to be treated. This allows maximum exposure of the tumor to radiation being emitted by the energy emitting source, whilst avoiding unnecessary and undesired exposure of healthy tissue surrounding the tumor.

Furthermore the treatment method according to the invention also implements repeating steps G-H-I for at least a further longitudinal catheter bore of said endorectal catheter probe. This further improves the final radiation treatment to be performed as the radiation being emitted by the energy emitting source at its several dwell positions and during the corresponding dwell times in the several catheter bores is directed directly to the tumor with an overall radiation dose distribution delivered being conformal to the tumor's geometry.

BRIEF DESCRIPTION OF THE INVENTION

Figure 2:
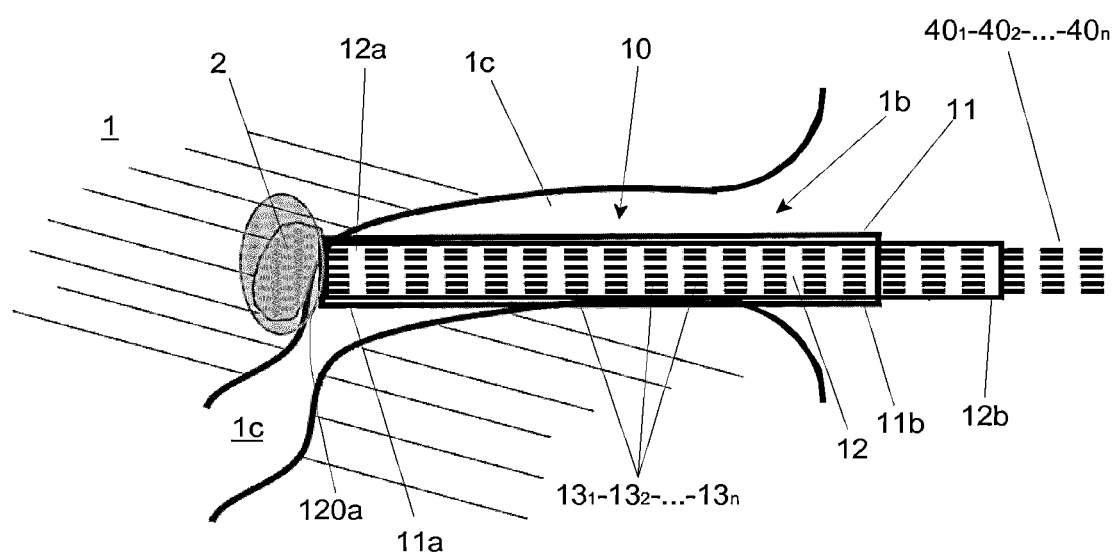
Figure 3:
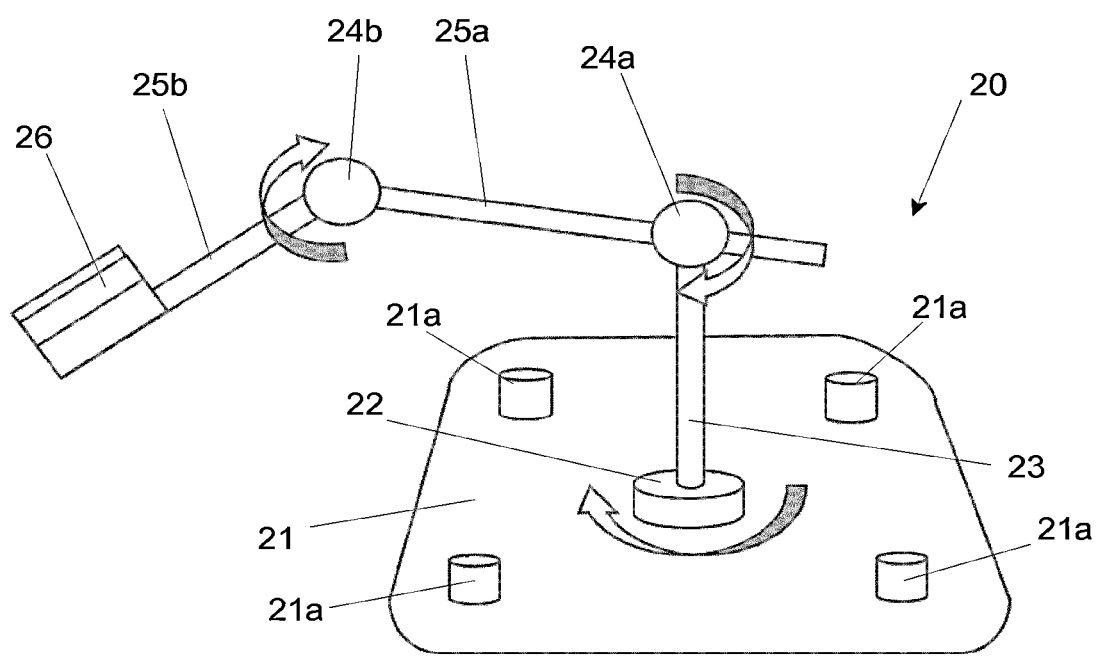
Figure 4:
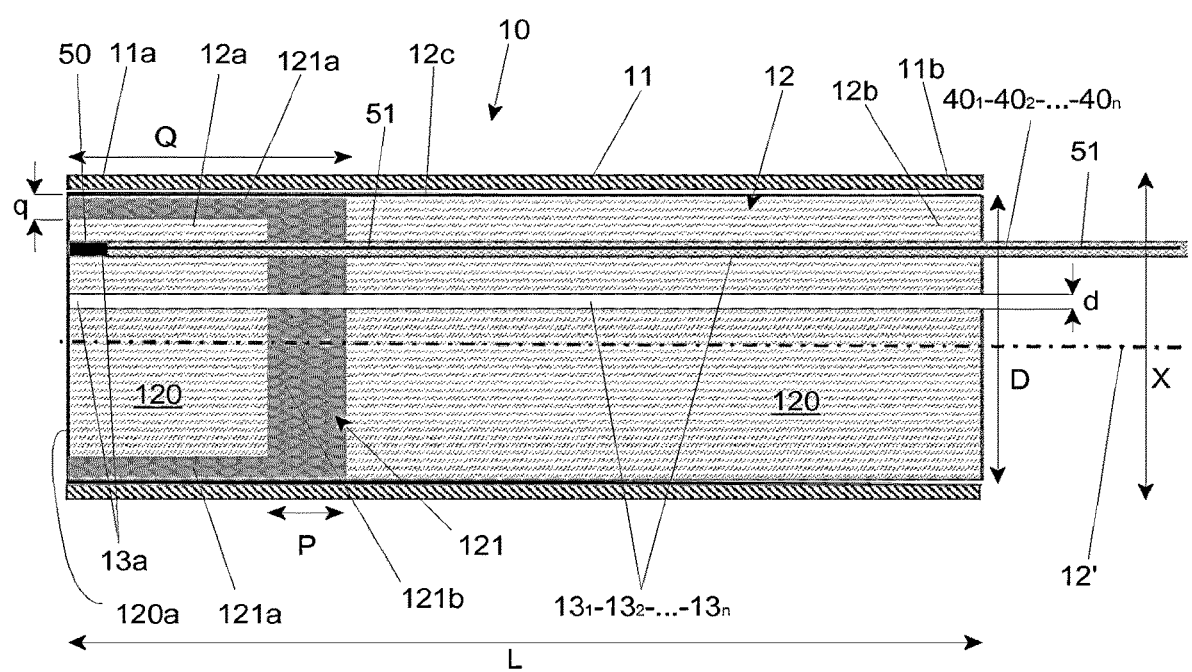
Figure 5A:
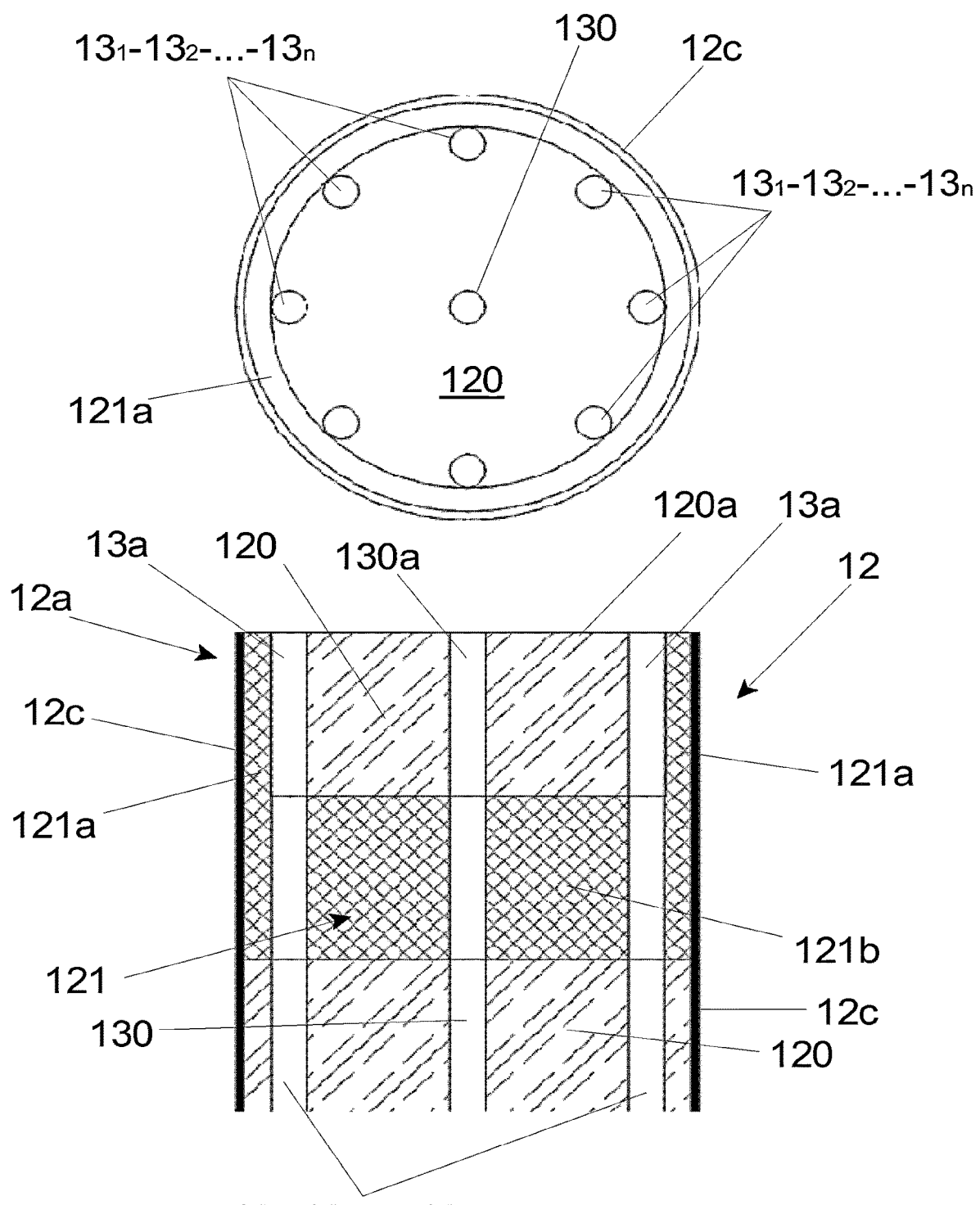
Figure 5B:
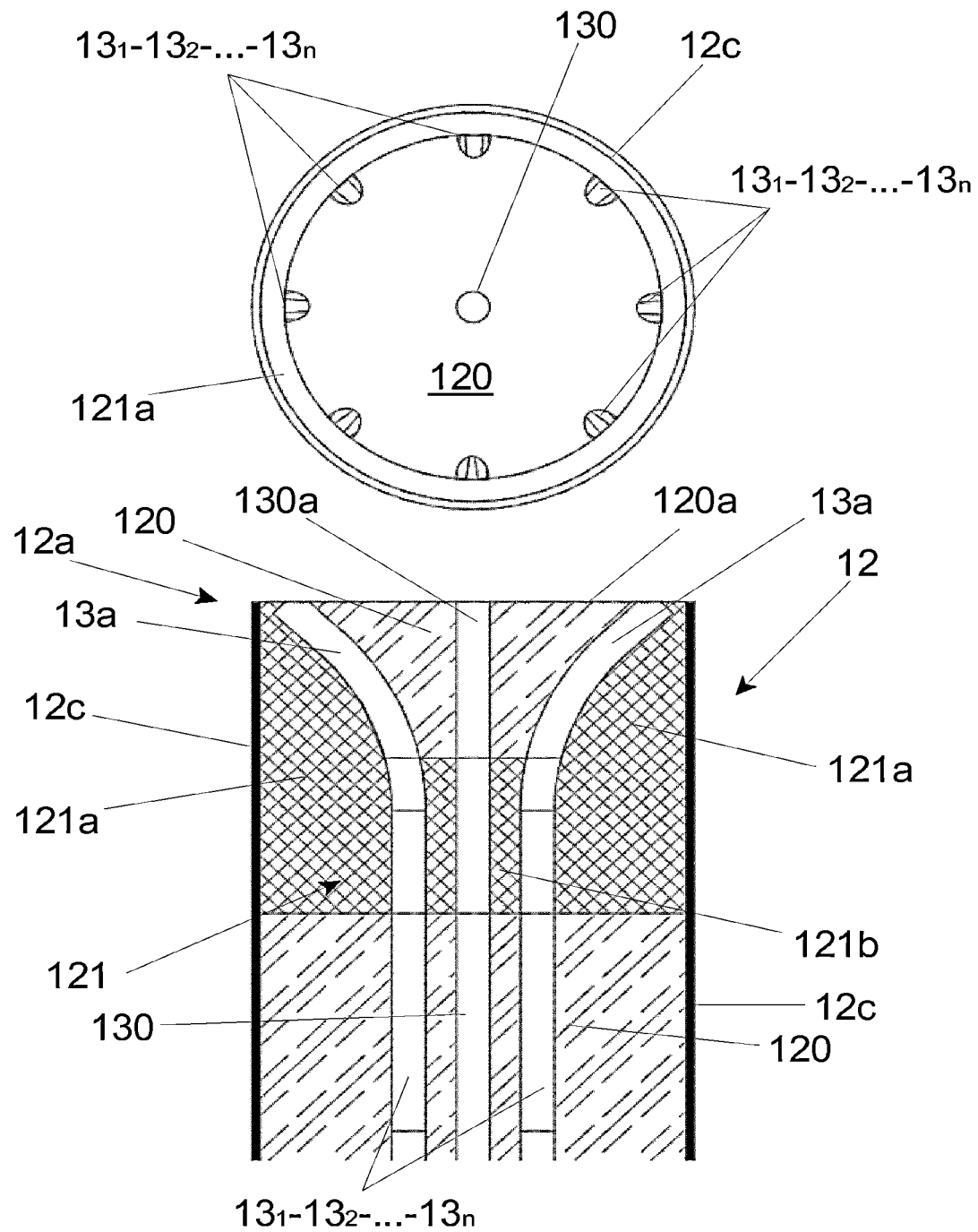
Figure 6A:
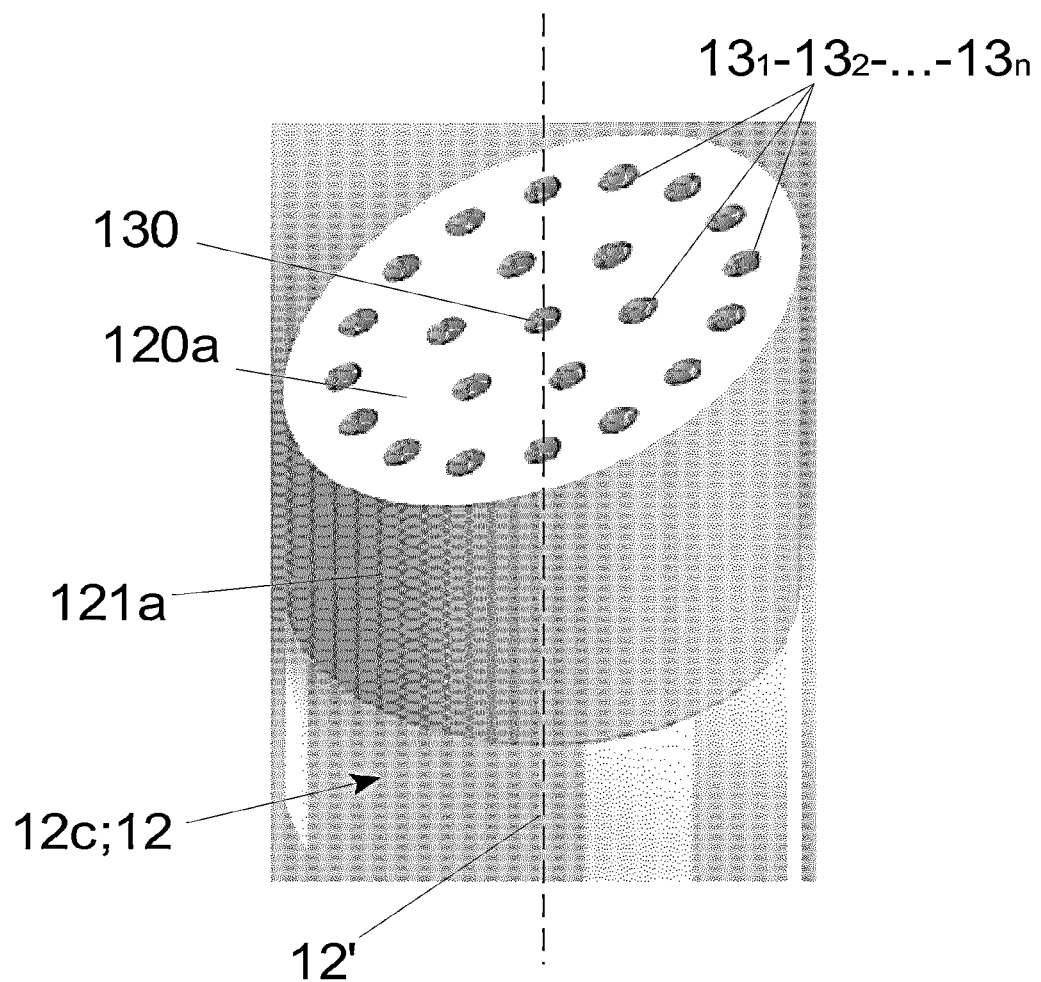
Figure 6B:
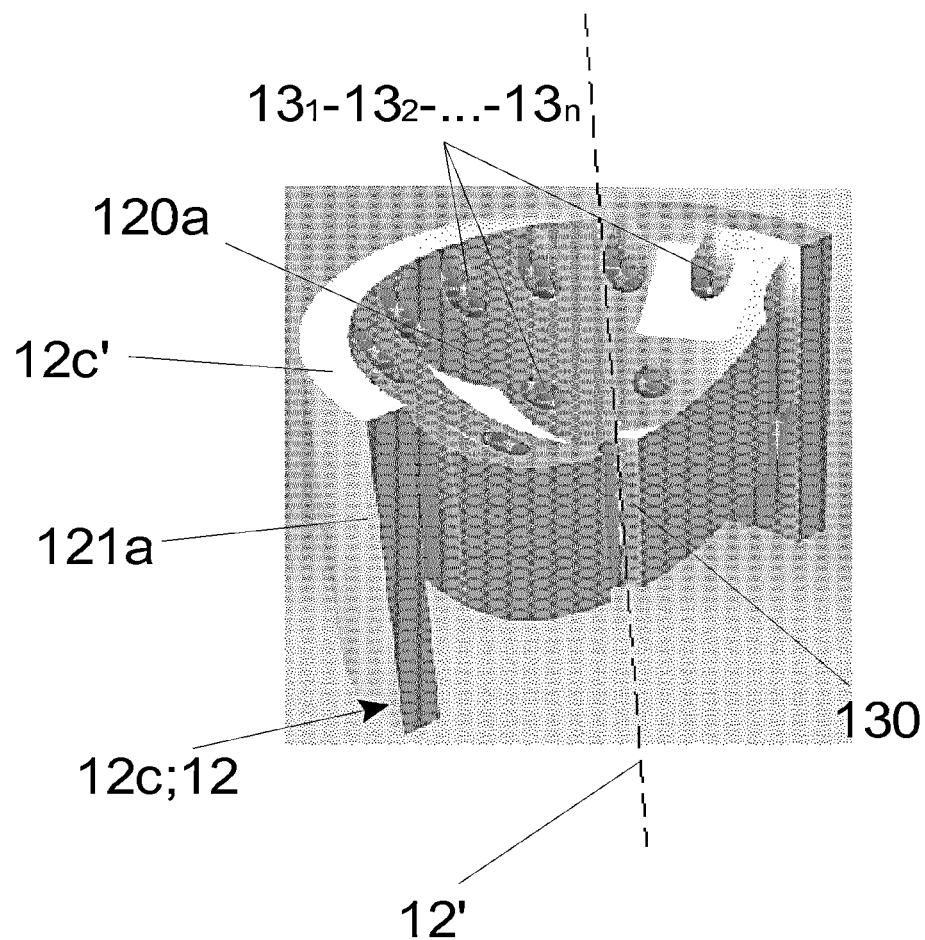
Figure 7A:
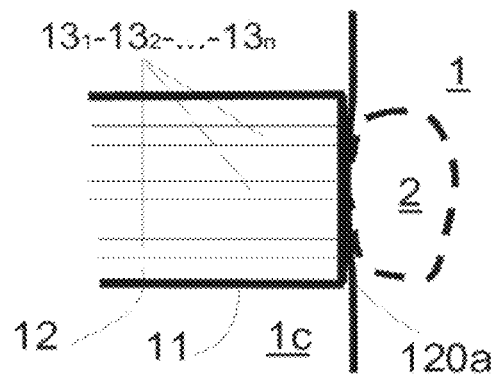
Figure 7B:
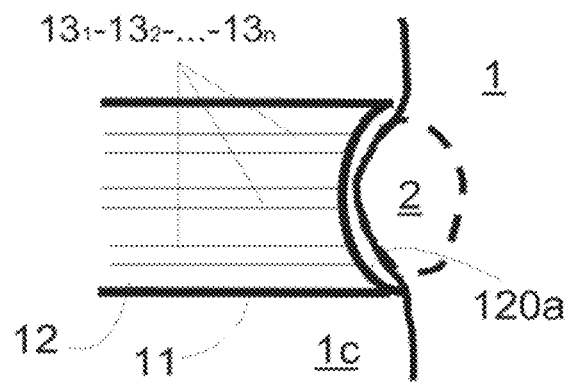
Figure 7C:
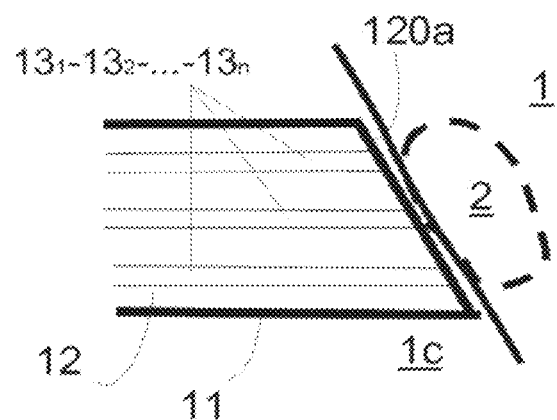

The invention will now be described in more detail with reference to the accompanying drawings, which drawings show in:

FIG. 1 a schematic depiction of a patient being treated with an endorectal probe device according to the invention interconnected to an afterloading apparatus;

FIG. 2 a detailed view of the endorectal probe device according to the invention positioned in the rectum of a patient;

FIG. 3 a clamping device for fixating the endorectal probe device according to the invention relative to the patient;

FIG. 4 a detailed view of an embodiment of an endorectal probe device according to the invention;

FIGS. 5A and 5B further embodiments of an endorectal probe device according to the invention;

FIGS. 6A and 6B further embodiments of an endorectal probe device according to the invention;

FIGS. 7A-7B-7C detailed views of endorectal probe devices according to the invention positioned in the rectum of a patient in dependence of the shape and location of the colorectal cancerous tumor;

FIGS. 8A-8I detailed views of endorectal probe devices according to the invention.

DETAILED DESCRIPTION OF THE INVENTION

For a better understanding of the invention like parts in the drawings are denoted with identical reference numerals.

In the detailed description below as well as in the claims various parts are denoted with the classification "proximal" and "distal". These classifications are to be considered in relation to the location of the colorectal cancerous tumor to be treated. Hence the classification "proximal" is to be understood as meaning "closest to the tumor to be treated" or "in a direction towards the location of the tumor". Similarly "distal" is to be understood as meaning "farthest from the tumor to be treated" or "in a direction away from the location of the tumor".

FIG. 1 shows in very schematic form various elements of a radiation treatment set-up for treating a colorectal cancer tumor inside the rectum of a patient with radiation using an endorectal probe device according to the invention interconnected to an afterloading apparatus.

A patient 1 is shown placed in an all-four position with his/her knees 1a on a treatment table 5, with the torso 1d of the patient 1 being supported by a support rest or support cushion 6. Alternatively the patient 1 rests with his/her torso 1d directly on the knees 1a, resulting in the anal opening 1b being more open for the insertion of the endorectal probe device 10. Fixedly connected to the treatment table 5 is a clamping device 20 for fixedly positioning and orientating an endorectal probe device 10. The endorectal probe device 10 according to the invention is inserted with its proximal device end 10a via the anus 1b into the rectum canal 1c. The endorectal probe device 10 is placed with its proximal device end 10a against a colorectal cancer tumor indicated with reference numeral 2. The colorectal cancer tumor 2 has developed in the rectum tissue wall and is to be treated by internally applying radiation, also called contact $^{192}$Ir/gamma/HDR brachytherapy, using the endorectal probe device 10 according to the invention.

It is known in the medical field to use afterloading apparatuses (or afterloaders) for the brachytherapy treatment of cancerous tumors using radioactive sources having an intensity greater than that, which can safely be handled. Remote afterloaders are devices generally used in the cancer treatment field to accurately advance and retract a flexible wire (the source wire) containing an energy emitting source over a specified distance for a specific time period. The energy emitting source is often a gamma radiation emitting source, such as a $^{192}$Ir source.

In FIG. 1 the afterloading apparatus 30 is depicted in a very schematic manner, but in general may comprise a base, which is preferably placed on wheels, a pedestal and a head. The head is vertically adjustable with respect to the pedestal by means of an adjustment mechanism. Usually the base or pedestal can be positioned manually in a desired location relative to the patient to be treated.

The head contains a flexible simulation or test ("dummy") wire for testing purposes and a flexible source wire with the energy emitting source, as well as specific control and transport mechanisms to operate both types of wires, as well as a radiation shielded housing for the radiation emitting source. The radiation shielded housing, in which the radiation emitting source is stored in between treatments, prevents unnecessary exposure of radiation towards the environment, in particularly to medical personal and the patient.

The medical procedure according to the invention initiates with placing the afterloading apparatus 30 near the patient 1 to be treated. Prior to the radiation treatment the endorectal probe device 10 is inserted into the rectum and against the tumor 2 to be treated. The endorectal probe device 10 is interconnected to the afterloading apparatus 30 by means of multiple (flexible) closed catheter tubes $40_1$-$40_2$- . . . -$40_n$ (also indicated as "guide tubes"), each catheter tube $40_1$-$40_2$- . . . -$40_n$ being guided in a corresponding catheter bore $13_1$-$13_2$- . . . -$13_n$ of the endorectal probe device 10.

A typical number n of catheter bores $13_1$-$13_2$- . . . -$13_n$ and thus also the number of corresponding catheter or guide tubes $40_1$-$40_2$- . . . -$40_n$ amounts approx. n=2 till 25, but usually n=5 till 15 depending on the desired radiation treatment as pre-planned.

As explained in more detail with reference to FIGS. 2 and 4 the endorectal probe device 10 is composed of an endorectal tube 11 and an endorectal catheter probe 12. The endorectal tube 11 has a hollow elongated body with an internal hollow dimension, which is more or less conformal (in fact slightly larger than) to the outer dimensions of catheter probe 12. According to the initiating step of the method according to the invention the endorectal tube 11 is inserted with its proximal tube end 11a via the anus 1b into the rectum 1c towards and against or around the cancerous tumor 2 in the rectum wall to be treated. Due to the length of the endorectal tube 11, it's distal tube end 11b is exposed and sticks outside the patient's rectum 1b.

Due to the hollow configuration of the endorectal tube 11 as well as the transparent material of which the tube 11 is made, in a next method step according to the invention a visual check to be performed by the medical personnel is possible in order to ascertain the correct position of the proximal tube end 11a relative to the cancerous tumor 2 to be treated. According to a further step of the treatment method according to the invention a repositioning of the proximal tube end 11a is possible until the proximal tube end 11a is properly placed against or more preferably around the cancerous tumor 2. After the visualizing step and if necessary the repositioning step according to the invention, in a subsequent step the distal tube end 11b of the endorectal tube 11 is then fixated relative to the patient 1 and the treatment table 5 by means of the clamping device 20 (explained further).

In a subsequent step, the catheter probe 12 is then slid with its proximal catheter probe end 12a in longitudinal direction in the hollow endorectal tube 11. Due to the proper orientation and alignment of the endorectal tube 11 relative to the cancerous tumor 2, also the catheter probe 12 is properly aligned, in particular as the outer dimensions of the catheter probe 12 are more or less conformal to the inner dimensions of the hollow endorectal tube 11. As such no play exists between both probe device elements 11 and 12 and the proximal catheter probe end 12a abuts or comes in direct contact with the tumor 2 to be treated.

Likewise the distal catheter probe end 12b is exposed outside the patient's rectum 1b and in a next step, the distal catheter probe end 12b is fixated by the clamping device 20 against undesired movements, and misalignments, which might adversely affect the radiation treatment to be performed.

Following the fixating of the endorectal probe device 10 (the assembly of the endorectal tube 11 and the endorectal catheter probe 12) relative to the patient 1 and the treatment table 5 the guide tubes $40_1$-$40_2$- . . . -$40_n$ are connected to the source wire opening (or a multiple of source wire openings) of the afterloading apparatus 30. Prior to the treatment the passage way of each guide tube $40_1$-$40_2$- . . . -$40_n$ until within the catheter bores $13_1$-$13_2$- . . . -$13_n$ is checked ("cleared") using the test ("dummy") wire (not shown), which is advanced and retracted from and thru the (head of the) afterloading apparatus into each guide tube $40_1$-$40_2$- . . . -$40_n$.

Once it has been ascertained that all guide tubes $40_1$-$40_2$- . . . -$40_n$ are clear and unblocked, the source wire drive means (not shown) present in the (head of the) afterloading apparatus 30 are activated for advancing the source wire (reference numeral 51 in FIG. 2) together with the energy (radiation) emitting source 50 (see also FIG. 2) through an internal guidance path within the afterloading apparatus 30, through the source wire opening and through one of the guide tubes $40_1$-$40_2$- . . . -$40_n$ connected to this source wire opening until into the corresponding catheter bore $13_1$-$13_2$- . . . -$13_n$ in the endorectal probe device towards an pre-determined position (the dwell position) within the relevant catheter bore near the tumor 2 to be treated.

Subsequently the radiation source 50 delivers a therapeutic, predetermined dose of radiation to the tumor during specific pre-planned periods of time (the dwell time). See also FIG. 2. The radiation is emitted towards the tumor under the principals of radioactive decay of radioactive material. After the radiation treatment the source wire drive means retract the source wire 51 together with the radiation source 50 back through the guide tube $40_1$-$40_2$- . . . -$40_n$ into the (head of the) afterloading apparatus 30.

Subsequently the source wire 51 can be advanced through another guide tube $40_1$-$40_2$- . . . -$40_n$ towards a different catheter bore $13_1$-$13_2$- . . . -$13_n$ and towards a subsequent different dwell position (or several dwell positions within the same catheter bore) near or against the tumor to be treated. Thus dependent on the necessary pre-planned radiation treatment it is possible to perform multiple treatment sessions with the same radioactive source at multiple, different treatment (dwell) positions within the rectum 1c of the patient 1.

FIG. 3 depicts an example of a clamping device 20 for use in cooperation with an endorectal probe device 10 according to the invention. The clamping device 20 is composed of a base plate 21 which is to be positioned on the flat surface of the treatment table 5 as shown in FIG. 1. Base plate 21 can be connected to the table 5 using suitable connecting means 21a which can be standardized for general hospital use.

Base plate 21 is provided with a rotating hinge connector 22 which supports a vertical support post 23. The vertical support post 23 is allowed to rotate around its own longitudinal direction and is provided with a first ball hinge 24a. First ball hinge 24a supports a first support bar 25a, which in turn is connected with a second ball hinge 24b. Second ball hinge 24b is subsequently connected to a second support bar 25b to which a support clamp element 26 is mounted.

It will be clear that in another embodiment the clamping device 20 may only comprise the first support bar 25a connected to the first ball hinge 24a, with the support clamp element 26 being mounted to the first support bar 25. Thus in that other embodiment the second ball hinge 24b and second support bar 25b are obviated.

It will be clear that the embodiment of the clamping device as shown in FIG. 3 has more degrees of freedom compared to the embodiment where the second ball hinge 24b and the second support bar 25b are obviated.

In the clamping device 20 as depicted in FIG. 3, the degrees of freedom consists of a rotation movement via rotating hinge connector 22 of the vertical support post 23 around its longitudinal orientation as well as degrees of freedom of the two ball hinges 24a and 24b. As such the support clamp element 26 can be properly positioned relative to the patient (see FIG. 1). Support clamp element 26 clamps (fixates) both the distal tube end 11b and the distal catheter probe end 12b, which are exposed outside the rectum 1c of the patient 1.

In FIG. 2, in combination with FIG. 4, the endorectal probe device 10 consists of two element parts, being the endorectal tube 11 and the endorectal catheter probe 12. The endorectal tube 11 is inserted with its proximal tube end 11a via the anus 1b into the rectum 1c and placed against or around the tumor 2 to be treated.

The endorectal tube 11 is preferably made of a transparent material, in particular a transparent plastic which allows— also due to its hollow configuration—a visual inspection of its position within the rectum 11c with respect to the tumor 2 to be treated. Upon visual inspection by the medical personnel the endorectal tube 11 can be repositioned by manually handling the distal tube end 11b exposed from the anus 1b and by maneuvering the proximal tube end 11a in such manner until the proximal tube end 11a is positioned against and preferably around the cancerous tumor 2 in the rectum tissue wall. Positioning the proximal tube end 11a against and preferably around the cancerous tumor 2 is further improved due to the fact that the hollow endorectal tube 11 is also open at its proximal tube end 11a.

As a proper visual inspection of the proximal tube end 11a relative to the cancerous tumor 2 can also be established by means of the hollow feature of the endorectal tube 11, the endorectal tube 11 can also be made from a non-transparent material, in particular from a metal material. The use of a metal material provides rigidity and stability of the endorectal probe device 10 during the radiation treatment, the metal material also provides a shielding against radiation emitted in undesired directions towards healthy tissue regions.

As the proper orientation of the endorectal tube 11 relative to the cancerous tumor 2 is ascertained, the endorectal tube 11 is fixated using the clamping device 20 (see FIG. 3) by coupling the exposed distal tube end 11b with the support clamp element 26 and subsequently locking the respective vertical hinge connector 22 and the first and second ball hinges 24a and 24b, thus preventing any unwanted displacement and reorientation of the endorectal tube 11 with respect to the cancerous tumor 2.

Catheter probe 12 is subsequently inserted with its proximal catheter probe end 12a via the fixated distal tube end 11b into the hollow endorectal tube 11 towards the cancerous tumor 2. As the proximal tube end 11a is properly placed against and preferably around the cancerous tumor 2 likewise the proximal catheter probe end 12a of the catheter probe 12 will abut against the tumor 2. Unlike the open proximal tube end 11a, the proximal catheter probe end 12a is closed and as such the closed proximal probe end face 120a abuts and contacts the cancerous tumor 2 in a direct manner.

The catheter probe 12 is provided with multiple catheter bores $13_1$-$13_2$- . . . -$13_n$ which catheter bores extend in longitudinal orientation, one of these catheter bores coinciding with the longitudinal axis 12' (central catheter bore 130). As clearly shown in FIGS. 5A-5B and 6A-6B the number n of catheter bores 130, $13_1$-$13_2$- . . . -$13_n$ can be 2 till 25 and preferably 5 till 15. The plurality of n catheter bores can be arranged in an equidistant manner around the central axis 12' (see FIG. 4, FIGS. 5A-5B and FIGS. 6A-6B) of the elongated body 12 and in particular in a circle wise manner. In particular the plurality of longitudinal catheter bores $13_1$-$13_2$- . . . -$13_n$ can be arranged in a first group in a circle close to the outer periphery 12c of the elongated body 12. See FIGS. 5A and 5B.

Also a further, second group of longitudinal catheter bores can be arranged in a circle, which is concentric to the circle formed by the first group of catheter bores. Such configuration is for example disclosed in the embodiments depicted in FIGS. 6A and 6B. Likewise the catheter probe 12 can be provided with a central catheter bore 130 with which coincides with the longitudinal axis 12' of the elongated body 12. See FIGS. 5A-5B and 6A-6B.

FIG. 4 shows the cross section of the endorectal probe device 10 depicting the hollow endorectal tube 11 and the endorectal catheter probe 12 placed within the endorectal tube 11. It is observed that the inner dimensions of the open, hollow endorectal tube 11 are slightly larger than the outer dimensions of the solid elongated catheter probe 12. As such no or a limited amount of play is present between the endorectal tube 11 and the endorectal catheter probe 12.

Only for the sake of clarity two catheter bores 13 are depicted in FIG. 4. Both catheter bores 13 are positioned at a different radius relative to the longitudinal axis 12'. Unlike the embodiments as shown in FIGS. 5A-5B and 6A-6B the catheter probe 12 as shown in FIG. 4 lacks a central catheter bore 130 coinciding with the longitudinal axis 12'.

For illustration purposes only one of the catheter bores is provided with a catheter or guide tube $40_1$-$40_2$- . . . -$40_n$, which interconnects the catheter probe 12 (in particular the relevant catheter bore) were the afterloading apparatus (not shown). The catheter or guide tube $40_1$-$40_2$- . . . -$40_n$ fills the relevant catheter bore 13 completely until the closed proximal probe end face 120a and serves as a passage way for a source wire 51 which is provided at its proximal end with an energy emitting source 50. The energy emitting source 50 is preferably a radiation emitting source, such as $^{192}$Ir-source.

As the close proximal probe end face 120a is placed against the cancerous tumor (not shown) to be treated, said tumor will be exposed directly with radiation emitted by the energy emitting source 50 positioned within the guide tube $40_1$-$40_2$- . . . -$40_n$ at the dwell position within the catheter bore 13 as shown in FIG. 4. The exposure time or dwell time of the radiation emitting source 50 at the respective dwell position within the catheter bore 13 depends on the radiation treatment to be performed and is pre-calculated by the processing means or dosage planning calculation means of the afterloading apparatus 30.

Such radiation dosage plan is generated prior to the actual radiation treatment and is generated by the dosage plan processing means of the afterloading apparatus according to the invention based on information concerning the patient to be treated, in particular the sex and age of the patient as well as visual image information about the location and size of the tumor to be treated. The dosage plan as calculated also contains information on the overall radiation dose to be emitted, the type of energy emitting source to be used, as well as information on the identification and location of the multiple catheter bores 130, $13_1$-$13_2$- . . . -$13_n$ of the endorectal catheter probe 12 through which the energy emitting source 50 is to be inserted towards to tumor 2 to be treated.

Furthermore the dosage treatment plan as calculated contains information on all the dwell positions for each of the multiple catheter bores 130, $13_1$-$13_2$- . . . -$13_n$ at which the energy emitting source 50 is to be positioned as well as the relevant exposure or dwell time corresponding to each calculated dwell position within each catheter bore.

As such an overall treatment plan is devised based on which the patient (the tumor 2) is properly radiated by the energy emitting source 50, which is subsequently pushed from the afterloading apparatus 30 into each individual catheter bore 130, $13_1$-$13_2$- . . . -$13_n$ and positioned at each pre-calculated dwell position within the respective catheter bore for the corresponding pre-calculated dwell time. The radiation treatment plan thus calculated is executed, until the energy emitting source 50 has been positioned during the corresponding dwell time at all dwell positions in the relevant catheter bores 130, $13_1$-$13_2$- . . . -$13_n$, such that the calculated overall radiation dose distribution has been delivered to the tumor 2 irradiates the cross section of the tumor to be treated. By repeating the radiation treatment multiple times over a certain period of time, the tumor 2 irradiated multiple times, which will ultimately result in a complete response. Over exposure of healthy tissue to radiation is herewith mostly avoided as the latter side effect is undesired due to health issues.

The endorectal probe device 10 (assembly of the endorectal tube 11 and the endorectal catheter probe 12) has a longitudinal dimension L of preferably 200-250 mm, with an overall diameter X (of the endorectal tube 11) of 22-32 mm (thickness of the hollow endorectal tube wall is approx. 2 mm) whereas the outer diameter D of the endorectal catheter probe 12 amounts 20-30 mm with the inner diameter d of each catheter bore 130, $13_1$-$13_2$- . . . -$13_n$ of 2-3 mm.

Preferably the endorectal catheter probe 12 is transparent to visible light at also for the radiation used for effecting the radiation treatment, and made from a plastic material 120. As such the catheter probe material 120 does not adversely affect the radiation treatment by absorbing the radiation being emitted by the energy emitting source 50. However in order to prevent an undesired exposure of healthy tissue surrounding the cancerous tumor 2 certain parts of the endorectal tube 11 and/or the endorectal catheter probe 12 can be made of a material, which is opaque to the radiation emitted by the energy emitting source 50.

In particular the proximal tube end 11a can contain or can be made from a material which is opaque to the radiation emitted and as such said opaque part of the proximal tube end 11a will absorb the radiation being emitted in a radial direction relative to the longitudinal axis 12' of the endorectal catheter probe 12. In particular said part of the proximal tube end 11a can contain partly or can be made entirely from a radiation shielding material such as lead or tungsten with a shielding distance or length Q (see FIG. 4) seen in the parallel direction of the longitudinal axis 12' of approximately 20-25 mm.

As such it is avoided that radiation emitted by the energy emitting source 50 in a radial direction relative to the longitudinal axis 12' escapes or leaves the endorectal probe device 10 in radial orientation and as such exposure of the healthy rectum tissue directly adjacent to the endorectal probe device 10 is prevented. In fact only radiation emitted in a frontal direction, meaning in the direction of the closed proximal catheter probe end face 120a (parallel to the longitudinal direction of the axis 12') and in the direction to the cancerous tumor 2 is emitted.

Another embodiment of an endorectal probe device 10 having radiation shielding capabilities is depicted in FIG. 4. In this embodiment the endorectal catheter probe 12 is provided with an insert material 121 manufactured from a radiation shielded material (which is opaque to radiation). In particular the radiation shielding insert material 121 is manufactured e.g. from lead or tungsten and is composed of a concentric radiation shielding insert wall 121a which extends close to the outer circumferential surface 12c of the endorectal catheter probe 12 with a thickness q of approx. 2-5 mm, as well as in a concentric yet parallel direction to the longitudinal axis 12' over a distance Q of 20-25 mm starting from the closed proximal probe end face 120a towards the distal probe end 12b.

Similarly the radiation shielding insert 121 is provided with an insert part 121b shaped as a disc which extends perpendicular and in radial orientation to the longitudinal axis 12' across the cross section of the probe 12 and has a thickness P of 10-15 mm (seen in longitudinal direction).

As such the proximal catheter probe end 12a of the catheter probe 12 is provided with a radiation shielding insert 121 surrounding the proximal catheter bore ends 13a of the catheter bores 130, $13_1$-$13_2$- . . . -$13_n$. An energy emitting source 50 being positioned at a dwell position near the proximal catheter bore end 13a in one of the catheter bores 130, $13_1$-$13_2$- . . . -$13_n$ can only freely emit radiation via the closed yet unshielded against radiation proximal probe end face 120a in the direction of the tumor 2. The proximal catheter probe end 12a is shielded off against radiation emitted in a radial direction (by means of the concentric radiation shielding insert 121a) as well as in the longitudinal distal orientation (by means of the radially extended radiation shielding insert 121b).

Only radiation will be emitted by the energy emitting source 50 in a frontal direction, seen in the longitudinal direction of the catheter probe 12 towards the proximal end 12a thereof and directly towards the tumor 2 which contacts the closed proximal catheter probe end face (or surface) 120a. See also the embodiments of FIGS. 5a-5b and 6a-6b showing similar configurations of radiation shielding inserts 121a and 121b.

The closed proximal catheter probe end face 120a of the catheter probe 12 is preferably flat and perpendicular to the longitudinal axis 12' as depicted in FIG. 4 as well as in FIGS. 5A and 5B. This allows for a direct, frontal contacting of the tumor 2 with the flat proximal end face 120a of the catheter probe 12. See also FIG. 7A, depicting a flat closed proximal catheter probe end face 120a of the catheter probe 12 directly abutting the tumor 2, which tumor is located directly under the flat rectum wall 1. This flat shaped embodiment of a closed proximal catheter probe end face 120a of the catheter probe 12 is particular suitable in situations where the tumor 2 is located directly under the flat surface of the rectum wall without deforming the surface of the rectum wall.

However, depending on the anatomical orientation of the tumor 2 within the rectum and the associated radiation treatment to be performed the closed proximal catheter probe end face 120a of the catheter probe 12 can also exhibit an inclined orientation relative to the longitudinal axis or direction of the endorectal catheter probe 12. An embodiment wherein the closed proximal catheter probe end face 120a is inclined relative to the longitudinal axis 12' of the endorectal catheter probe 12 is depicted in FIG. 6A, combined with FIG. 7C in which the endorectal catheter probe 12 exhibits a closed proximal catheter probe end face 120a exhibiting an inclined end face orientation relative to the longitudinal axis. The inclined end face 120a allows for a proper positioning of the endorectal catheter probe 12 against the tumor 2 in situations where the rectum wall also exhibits an inclined tissue surface with respect to the longitudinal axis 12' of the endorectal catheter probe 12.

FIG. 6B depicts yet another geometry of the closed proximal catheter probe end face 120a of the endorectal catheter probe 12. In this embodiment the closed proximal catheter probe end face 120a of the endorectal catheter probe 12 exhibits a concave surface. This hollow or semi-spherical geometry of the closed proximal catheter probe end face 120a allows for a more accurate positioning of the proximal catheter probe end 12a of the endorectal catheter probe 12 against and around the tumor 2, in particular when the tumor 2 extends or bulges out of the rectum wall. See also FIG. 7B in which the hollow or semi-spherical geometry of the closed proximal catheter probe end face 120a captures and encloses the tumor 2 that in this patient bulges out of the rectum wall 1. The hollow concave geometry of the closed proximal catheter probe end face 120a of the catheter probe 12 insures a proper matching and accommodating of the proximal catheter probe end 12a around and over the tumor 2 and as such guarantees a proper direct frontal radiation of the tumor once the energy emitting source 50 is positioned within one of the catheter bores 130, $13_1$-$13_2$- . . . -$13_n$ near of at the closed catheter probe end surface 120a.

Preferably the plurality of catheter bores 130, $13_1$-$13_2$- . . . -$13_n$ extend parallel to each other throughout the overall longitudinal orientation of the catheter probe 12. These configurations of the catheter bores is for example depicted in FIG. 4, but also in FIG. 5A, and FIG. 6B.

Yet in another configuration the catheter bores 130, $13_1$-$13_2$- . . . -$13_n$ extend parallel to each other over the majority of the longitudinal orientation of the catheter probe 12 but said catheter bores $13_1$-$13_2$- . . . -$13_n$ diverge from each other near the proximal end 12a of the endorectal catheter probe 12. This embodiment is depicted in FIG. 5B where the several catheter bores $13_1$-$13_2$- . . . -$13_n$ extend parallel to each other and close to the central catheter bore 130, but they diverge within the proximal end part 12a which is enclosed by the radiation shielding inserts 121a-121b. It is to be noted that the central catheter probe 130 does not diverge but extends along the longitudinal axis 12' over the full length of the catheter probe 12.

Furthermore the embodiments of FIGS. 5A-5B depict one group of catheter bores $13_1$-$13_2$- . . . -$13_n$ which are arranged in an equidistance manner around the central axis 12'/the central catheter bore 130 in a circle wise manner close to the outer circumferential surface 12c of the catheter probe 12. The embodiments of FIGS. 6B and 6A depicts two groups of catheter bores $13_1$-$13_2$- . . . -$13_n$, one group being orientated around the central axis 12'/the central catheter bore 130 in a circle wise manner close to the outer surface 12c, whereas the other group of catheter bores is also arranged in an equidistance circle wise manner around the central bore 130, but inside (concentric to) the circle formed by the outer group of catheter bores.

Preferably the endorectal catheter probe 12 and its configuration of (groups of) plurality of longitudinal catheter bores 130, $13_1$-$13_2$- . . . -$13_n$ is rotational symmetric with respect to its longitudinal central axis 12'. As such its orientation within the endorectal tube 11 is independent. However both the endorectal tube 11 and the endorectal catheter probe 12 can be provided with alignment markings near or at their distal ends 11b and 12b, thus ensuring a correct positioning and orientation of the catheter probe 12 within the endorectal tube 11.

The cylindrical configuration of both the endorectal tube 11 and the endorectal catheter probe 12 also allows to a reorientation of the endorectal catheter probe 12 within the endorectal tube 11 by means of a rotational movement of the endorectal catheter probe 12 around its longitudinal central axis 12' by means of a manual handling by the medical personnel.

The endorectal catheter probe 12 is preferably manufactured using a 3D printing technique.

Detailed examples of endorectal probe devices according to the invention are depicted in of FIGS. 8A-8H. These embodiments show the several distinct configurations or shapes of the closed proximal catheter probe end face 120a of the proximal catheter probe end 12a of the endorectal catheter probe 12 positioning of against and around the tumor 2.

Figure 8A:
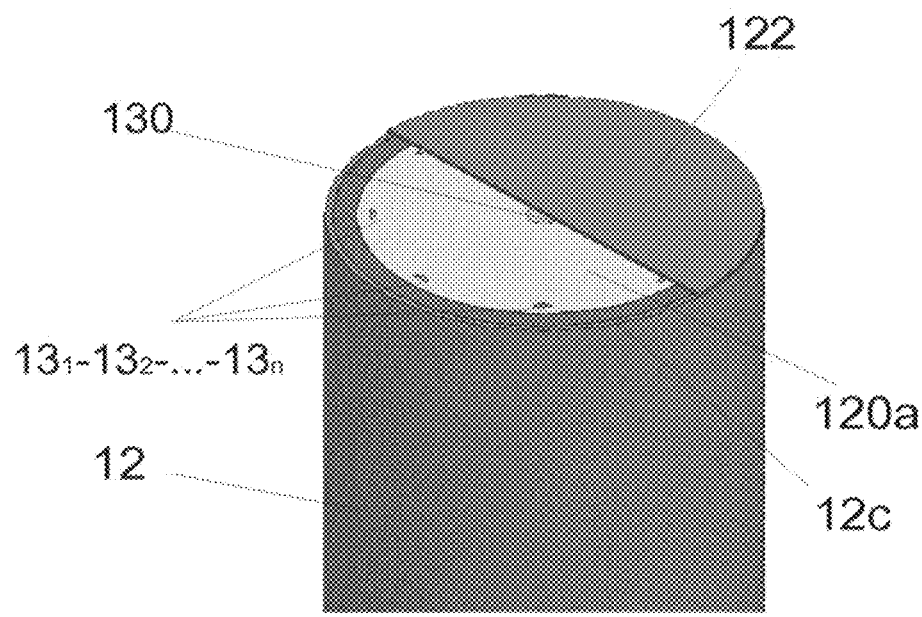
Figure 8B:
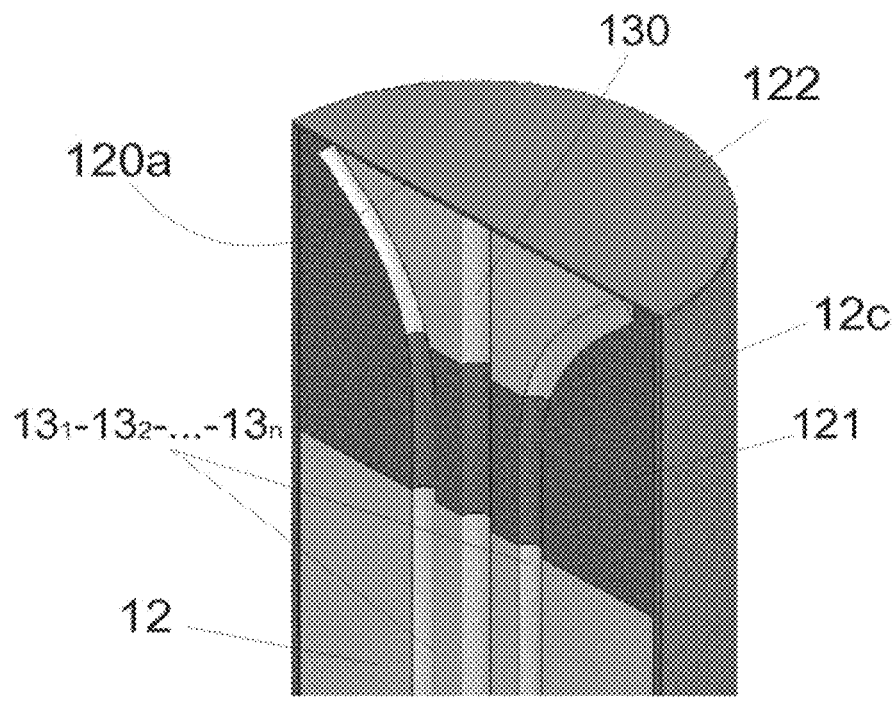

FIGS. 8A and 8B show two embodiments implementing a flat end face 120a, which is positioned perpendicular to the longitudinal axis 12' of the catheter probe 12. These embodiments allow for a frontal exposure of the tumor 2 with radiation, by placing the endorectal tube 11 in a frontal orientation directly against and surrounding the tumor 2, and subsequently inserting the endorectal catheter probe 12 inside the already positioned endorectal tube 11, such that the proximal catheter probe end 12a abuts with its flat end face 12 against the tumor 2 for effecting radiation treatment.

Figure 8C:
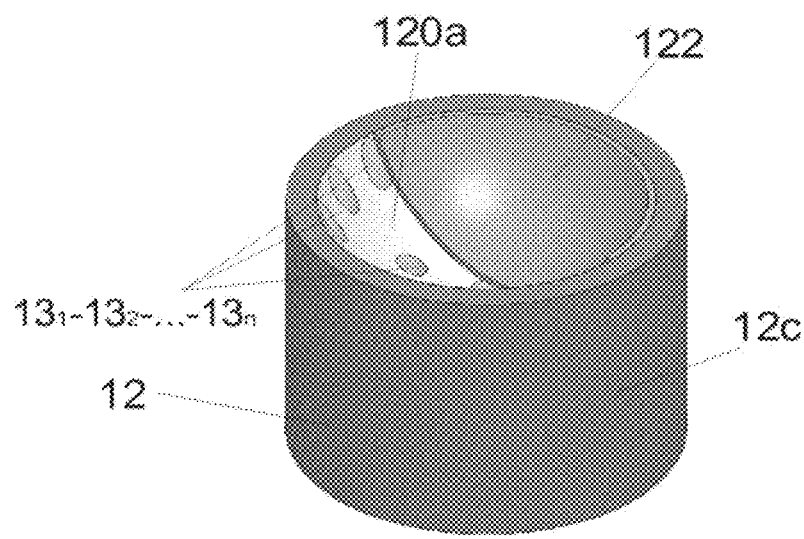

FIG. 8C depicts the proximal catheter probe end 12a of an endorectal catheter probe 12 exhibiting a concave surface. This hollow or semi-spherical geometry of the closed proximal catheter probe end face 120a allows for a more accurate positioning of the proximal catheter probe end 12a of the endorectal catheter probe 12 against and around the tumor 2, in particular when the tumor 2 extends or bulges out of the rectum wall.

Figure 8D:
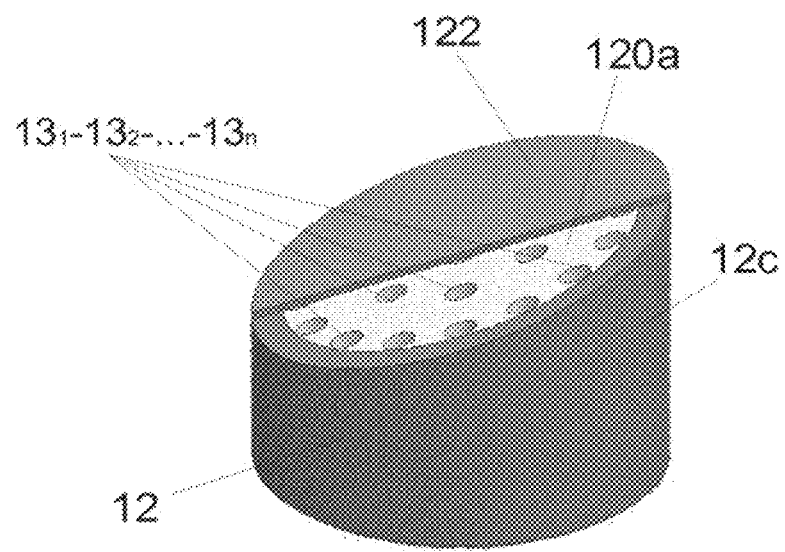

FIG. 8D depicts a closed proximal catheter probe end face 120a exhibiting an inclined end face orientation relative to the longitudinal axis. The inclined end face 120a allows for a proper positioning of the endorectal catheter probe 12 against the tumor 2 in situations where the rectum wall also exhibits an inclined tissue surface with respect to the longitudinal axis 12' of the endorectal catheter probe 12.

Figure 8E:
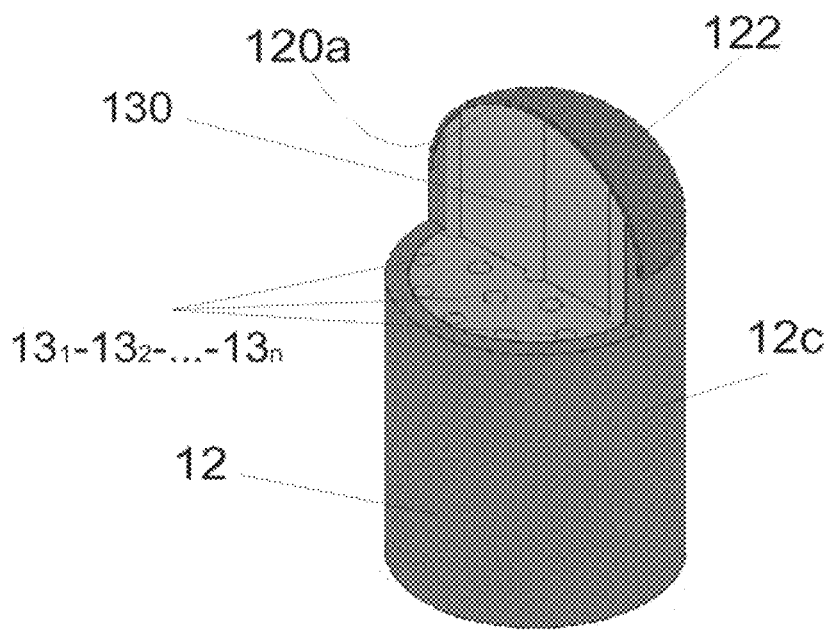

FIG. 8E depicts the proximal catheter probe end 12a of an endorectal catheter probe 12 exhibiting a convex or outwardly orientated semi-spherical surface. The embodiment of FIG. 8E is a combination of the embodiment of FIG. 8A as the convex end face 120a is positioned perpendicular to the longitudinal axis 12'. Also this embodiment of the endorectal catheter probe 12 allows for a frontal exposure of the tumor 2 with radiation, wherein the tumor 2 is located deeper below the rectum wall or has created an inner bulge in the rectum wall.

Figure 8F:
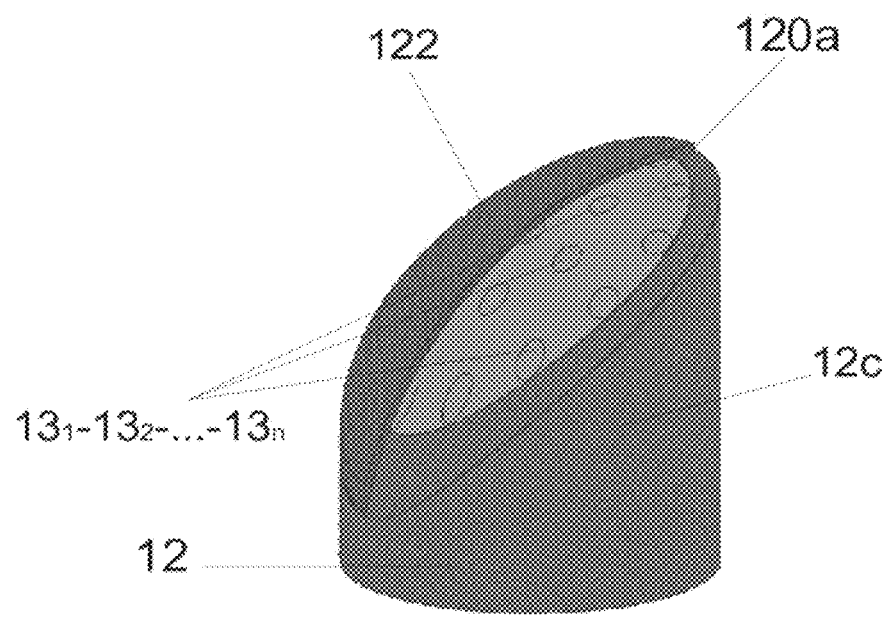

FIG. 8F depicts an endorectal catheter probe 12 exhibiting a combination of the inclined end face 120a of FIG. 8D together with a convex or outwardly orientated semi-spherical surface as depicted in FIG. 8E.

Figure 8G:
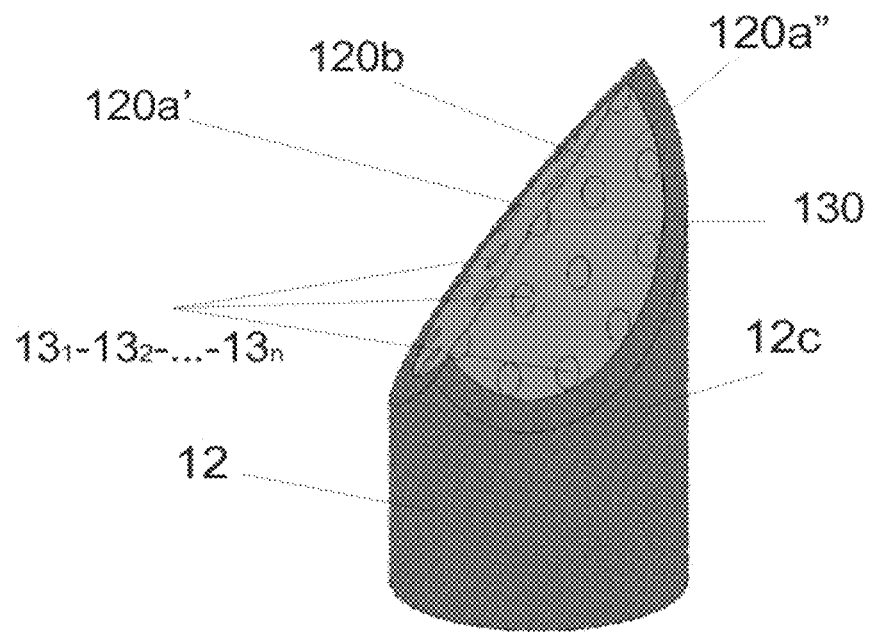

FIG. 8G depicts an endorectal catheter probe 12 exhibiting a three-dimensional end face being composed of two inclined end face parts 120a' and 120a" which are both inclined with respect to the longitudinal axis 12' of the probe 12. Furthermore the common boundary line or vertex line 120b is also inclined with respect to the longitudinal axis 12' allowing for a versatile end face configuration to be used in specific radiation treatments.

Figure 8H:
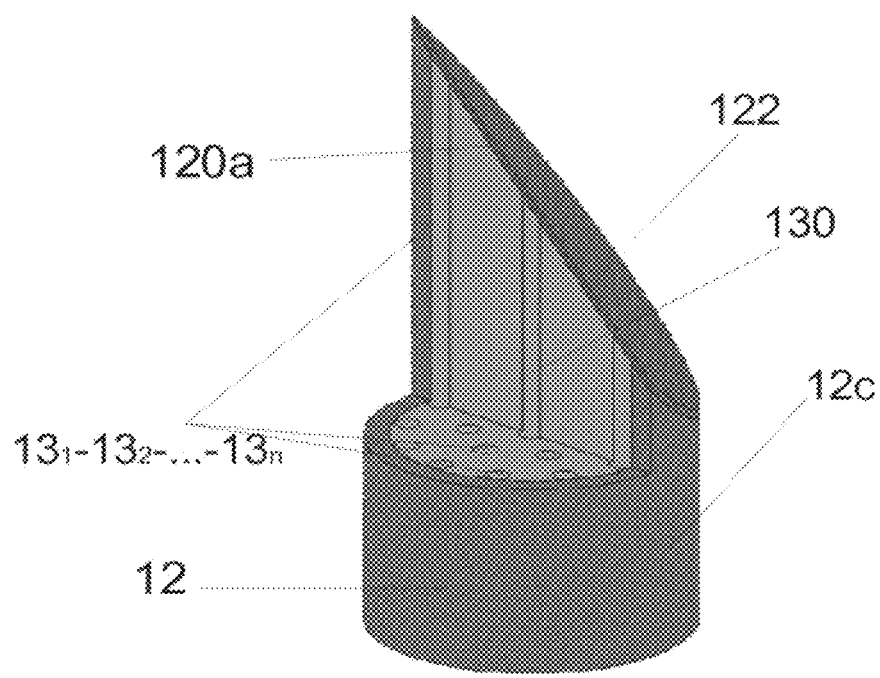

Similarly, the embodiment of FIG. 8H depicts an endorectal catheter probe 12 exhibiting an inclined end face 120a which is inclined in two orthogonal directions with respect to the longitudinal axis 12' of the probe 12 (as compared to the embodiments of FIGS. 6A and 8D whose end faces 120a are inclined in one orthogonal direction with respect to the longitudinal axis 12' of the probe 12).

Figure 8I:
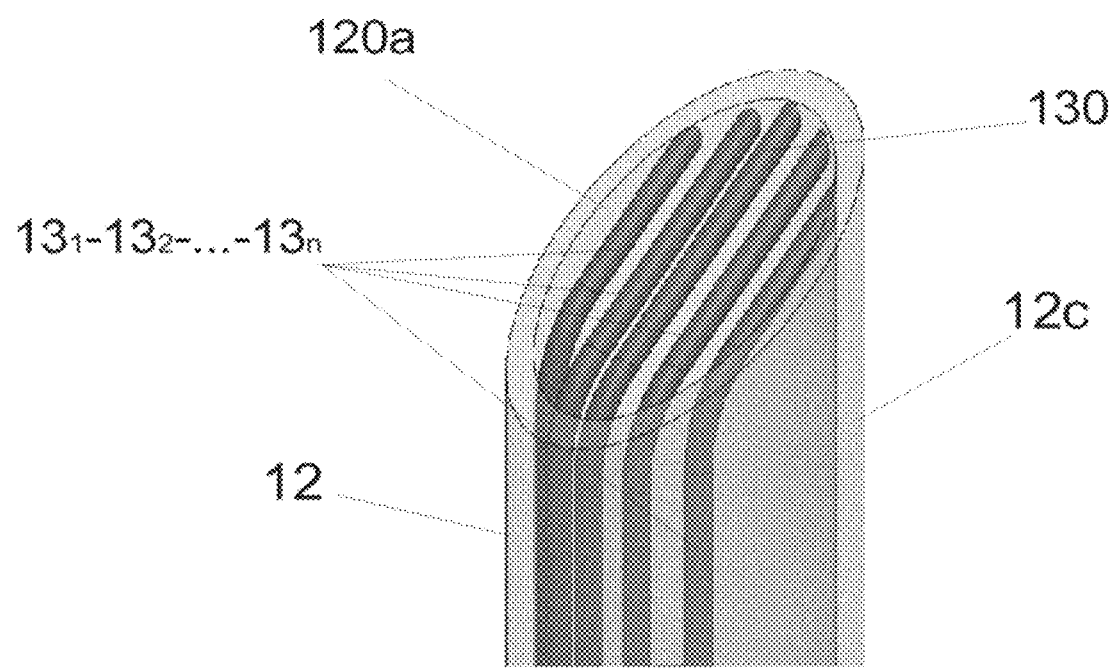

An alternative of the embodiment of FIG. 8D is shown in FIG. 8I. The inclined end surface 120a serves for placement against the tumor to be treated and the catheter bores 130, $13_1$-$13_2$- . . . -$13_n$ are positioned closely below and are running parallel to each other and parallel to the closed catheter probe end surface 120a. Herewith an inclined end surface 120a is obtained that can serve entirely as an energy emitting surface as the energy emitting source 50 can be positioned at different locations within the several catheter bores 130, $13_1$-$13_2$- . . . -$13_n$ and closely below the closed catheter probe end surface 120a at a close distance of the tumor to be treated. In the embodiment of FIG. 8I the inclined end surface 120a is shaped as a flat end surface, however in another version the inclined end surface 120a can also be shaped as a convex or outwardly orientated semi-spherical surface.

In all embodiments shown in FIGS. 8A-8I the proximal catheter probe end face 120a can be properly covered by a protective cover 122 for safety issues, which protective cover 122 can be made from a durable plastic material.

It is remarked that all embodiments of the distinct configurations or shapes of the closed proximal catheter probe end face 120a of the catheter probe 12 insure a proper matching and accommodating of the proximal catheter probe end 12a around and over the tumor 2 depending on the physique of the tumor in the rectum of the patient. Depending on the physique of the tumor 2 (size, dimensions, orientation, bulge in or bulge out with respect to the rectum wall) the proper catheter probe shape of configuration can be selected by the physician administering the radiation treatment.

The proper selection of the most effective probe configuration design guarantees a proper direct frontal radiation of the tumor once the energy emitting source 50 is positioned within one of the catheter bores 130, $13_1$-$13_2$- . . . -$13_n$ near of at the closed catheter probe end surface 120a.

In all treatment situations the endorectal tube 11 is placed directly against and around the tumor 2, and subsequently the properly selected endorectal catheter probe 12 is inserted in the positioned endorectal tube 11, such that the proximal catheter probe end 12a abuts with its specifically configured or shaped end face 12 against the tumor 2 for effecting radiation treatment.

REFERENCE NUMERAL LISTING 1 patient
1a leg/knee
1b anus
1c rectum
1d torso
2 tumor
5 support table
6 support rest or cushion
10 endorectal probe device
10a proximal probe device end
10b distal probe device end
11 endorectal tube
11a proximal tube end
11b distal tube end
12 endorectal catheter probe
12' longitudinal probe axis
12a proximal catheter probe end
12b distal catheter probe end
12c outer catheter probe surface
12c' proximal catheter probe end surface
120 catheter probe material
120a-120a'-120a" closed proximal catheter probe end face
120b vertex line
121 energy shielding insert material
121a concentric shielding wall
121b transverse shielding wall
122 shielding face of proximal catheter probe end surface
$13_1$-$13_2$- . . . -$13_n$ longitudinal catheter bore
13a proximal catheter bore end
130 central catheter bore 130a proximal central bore end
20 clamping apparatus
21 support plate
21a connecting means
22 rotating hinge connector
23 vertical support post
24a first ball hinge
24b second ball hinge
25a first support bar
25b second support bar
26 support clamp element
30 afterloading apparatus
$40_1$-$40_2$- . . . -$40_n$ catheter/guide tubes
50 energy emitting source
51 source wire

The invention claimed is:

1. An endorectal probe device comprising:
an endorectal tube;
an endorectal catheter probe having a distal probe end and a proximal probe end, the proximal probe end being arranged to be inserted into the endorectal tube towards a tissue of a patient, the proximal probe end includes an end face, the end face including at least one of a flat surface or a concave surface, the flat or concave surface being inclined relative to a longitudinal direction of the endorectal catheter probe; and
a radiation shielding insert within the endorectal catheter probe adjacent the proximal probe end, the radiation shielding insert including a disk and a radiation shielding wall coupled to the disk, the disk defining at least a portion of a plurality of longitudinal catheter bores extending from the distal probe end towards the proximal probe end.

2. The endorectal probe device of claim 1, wherein the radiation shielding insert is configured to shield radiation emitted in a radial direction.

3. The endorectal probe device of claim 1, wherein the radiation shielding insert is configured to shield the proximal probe end from radiation emitted in the longitudinal direction of the endorectal catheter probe.

4. The endorectal probe device according to claim 1, wherein the radiation shielding wall configured to shield radiation emitted in a radial direction.

5. The endorectal probe device according to claim 1, wherein the endorectal catheter probe further includes:
an elongated body extending between the distal probe end and the proximal probe end, the elongated body defining the plurality of longitudinal catheter bores extending from the distal probe end towards the proximal probe end.

6. The endorectal probe device according to claim 5, wherein the plurality of longitudinal catheter bores are arranged in an equidistant manner.

7. The endorectal probe device according to claim 6, wherein the plurality of longitudinal catheter bores are arranged around a central axis of the elongated body in a circle wise manner.

8. The endorectal probe device according to claim 5, wherein the plurality of longitudinal catheter bores extend parallel to each other through the elongated body.

9. The endorectal probe device according to claim 5, wherein the plurality of longitudinal catheter bores diverge from each other at a portion of the endorectal catheter probe.

10. The endorectal probe device according to claim 5, wherein the elongated body of the endorectal tube has a straight orientation.

11. The endorectal probe device according to claim 1, wherein the endorectal catheter probe is transparent to visible light and radiation used for effecting a radiation treatment.

12. The endorectal probe device according to claim 1, wherein the endorectal tube is made of a rigid material.

13. The endorectal probe device according to claim 1, wherein the proximal probe end is at least partly opaque to radiation for effecting a radiation treatment.

14. The endorectal probe device according to claim 1, wherein the endorectal catheter probe is movable in at least the longitudinal direction of the endorectal tube within the endorectal tube.

15. The endorectal probe device according to claim 1, further comprising:
a cover configured to cover the end face.

16. The endorectal probe device according to claim 1, further comprising:
a clamping device configured to fixate the endorectal catheter probe and the endorectal tube.

17. The endorectal probe device of claim 1, wherein the end face includes the flat surface.

18. The endorectal probe device of claim 1, wherein the end face includes the concave surface.

19. A system comprising:
an afterloading apparatus; and
the endorectal probe device of claim 1 coupled to the afterloading apparatus.

* * * * *